(12) United States Patent
Ma et al.

(10) Patent No.: US 7,965,814 B2
(45) Date of Patent: Jun. 21, 2011

(54) X-RAY DEVICE

(76) Inventors: Yue Ma, Beijing (CN); Yan Zhou, Beijing (CN)

( * ) Notice: Subject to any disclaimer, the term of this patent is extended or adjusted under 35 U.S.C. 154(b) by 219 days.

(21) Appl. No.: 11/817,470

(22) PCT Filed: Mar. 1, 2005

(86) PCT No.: PCT/CN2005/000253
§ 371 (c)(1),
(2), (4) Date: Sep. 10, 2008

(87) PCT Pub. No.: WO2006/092078
PCT Pub. Date: Sep. 8, 2006

(65) Prior Publication Data
US 2009/0010389 A1    Jan. 8, 2009

(51) Int. Cl.
*G01N 23/04* (2006.01)
(52) U.S. Cl. .......................... 378/62; 378/122
(58) Field of Classification Search ............ 378/62, 378/93, 95, 101, 111, 112, 114–117
See application file for complete search history.

(56) References Cited

U.S. PATENT DOCUMENTS

| | | | |
|---|---|---|---|
| 4,562,464 A | 12/1985 | Kurihara | |
| 5,812,629 A * | 9/1998 | Clauser | 378/62 |
| 6,554,472 B1 * | 4/2003 | Dietz et al. | 378/197 |
| 6,633,775 B1 * | 10/2003 | Bernard | 600/428 |
| 6,901,129 B2 * | 5/2005 | Tachizaki et al. | 378/4 |
| 6,937,696 B1 * | 8/2005 | Mostafavi | 378/95 |
| 7,085,351 B2 * | 8/2006 | Lu et al. | 378/122 |
| 7,440,539 B2 * | 10/2008 | Danielsson et al. | 378/37 |
| 7,490,085 B2 * | 2/2009 | Walker et al. | 707/10 |

FOREIGN PATENT DOCUMENTS

| | | |
|---|---|---|
| CN | 2151483 | 12/1993 |
| CN | 2542207 | 4/2003 |
| CN | 2542207 Y | 4/2003 |
| CN | 1511498 | 7/2004 |

OTHER PUBLICATIONS

International Search Report prepared by The State Intellectual Property Office, the P.R. China dated Dec. 8, 2005; PCT/CN2005/000253; Applicant, Yu Ma and Yan Zhou.
International Application No. PCT/CN2005/000253, International Preliminary Report on Patentability and Written Opinion (including English translation).

* cited by examiner

*Primary Examiner* — Jurie Yun
(74) *Attorney, Agent, or Firm* — Sheridan Ross P.C.

(57) ABSTRACT

An X-ray device which is especially applicable to the X-ray imaging for child at the age of 0-3 is provided. The X-ray device can use the X-ray tube (10) which uses the molybdenum target or rhodium target (12) to produce the soft X-ray by the tube voltage between 25 and 50 kV. The synchronous-exposing equipment contained in the X-ray device may identify the still status and the breath, pulse status suitable for exposure of the child, automatically select the optimal exposing time so that it can acquire a clear X-ray image through only one X-ray exposure, thus prevent the human body from the needless X-ray radiation caused by the multiple X-ray exposures, and also improve the service efficiency of the equipment.

14 Claims, 9 Drawing Sheets

X-RAY DEVICE

FIELD OF THE INVENTION

The invention relates to an X-ray device, in particular to a pediatric special purpose soft X-ray device.

BACKGROUND OF THE INVENTION

Existing general X-ray devices employ a tube voltage ranged from 50 kV to 125 kV. Energy in such a range is too high for a child at age of 0-3. Since a child's body is small and his/her bones are not calcified completely, substantially all X-ray transmits through the body, thus it is difficult to obtain a clear X-ray photograph. A special purpose X-ray device for the mammography diagnose employs a typical tube voltage ranged from 20 kV to 32 kV, which is not applicable for the child at the age of 0-3 years.

In addition, a moving body would produce a moving artificial image on the film during photographing, which causes the image unclear. It is difficult for the child at the age of 0-3 to keep still status as an adult during an X-ray irradiation measurement. Therefore, a general X-ray device can not obtain the clear X-ray photograph of a child due to the child's frequent movement. Similarly, breath and heart beat would also affect the definition of the X-ray irradiation image.

Furthermore, since the child is in the stage of rapid growth, there are a lot juvenile cells in the body, which are more sensitive to ionizing irradiation, the X-ray are harmful to the child especially. Therefore, it is necessary for the child to avoid a large area of X-ray irradiation so as to reduce received dose of unnecessary X-ray irradiation. Thus, it should only irradiate necessary parts and shield other parts from being irradiated. Moreover, X-ray technicians, doctors and parents of a sick child should avoid the X-ray radiation. However, such an X-ray irradiation protection is not considered for a general X-ray device.

SUMMARY OF THE INVENTION

One object of the present invention is to provide an X-ray device which is applicable to X-ray imaging for a child at age of 0-3. Another object of the present invention is to provide an X-ray device capable of performing synchronous exposure control.

To achieve above objects, the present invention provides an X-ray device, including: an X-ray tube, wherein a distance between a filament and an anode target surface of the X-ray tube has a range of 13 ~15 mm or a distance between a filament cage and the anode target surface of the X-ray tube has a range of 8~10 mm, which produces X-ray at a tube voltage between 25-50 kV so as to be used in X-ray imaging for child at age of 0-3.

Further, in the X-ray device of the present invention, small-bore collimators are disposed respectively on an X-ray outlet along the direction of X-ray radiation and under a table on which a subject of a human body is placed, and a collimation label is disposed on the table so that the X-ray is collimated by the two small-bore collimators and the collimation label. Thereby, by measuring absorptivities of the X-ray with two different energy $I_{01}$, $I_{02}$ passing through bones and soft-tissues and the absorbance attenuated energy $I_1$, $I_2$, a bone density MB (with unit of g/cm$^2$) can be calculated as follows:

$$M_B = (u_{1S}J_2 - u_{2S}J_1)/(u_{1S}u_{2B} - u_{2S}u_{1B})$$

$$J_1 = \ln(I_{01}/I_1), J_2 = \ln(I_{02}/I_2)$$

where the subscript 1 and 2 represent related values corresponding to the two different incident energy respectively, $u_B$, $u_S$ are absorbance attenuated coefficients of the bone B and the soft-tissue S respectively.

The X-ray device of present invention further includes: an X-ray guard, wherein disposed between an outlet of the X-ray tube and a subject of a human body is an extendable lead protection cavity, which extends to touch the part of the human body being irradiated such that the X-ray only radiates within a range of the part being irradiated, and the other parts are protected from the X-ray by the lead protection cavity. Thus, it makes the leakage radiation and the scattered radiation smaller and has a better radiation protection than the normal X-ray device.

The present invention further provides a synchronous-exposure control system for an X-ray device, including: a detecting device to automatically identify status of a subject of a human body and output an trigger signal when determining that the human body is in a preset still status or a relative stable status according to the identified status of the human body; a synchronous-exposure controller to perform automatic synchronous-exposure according the trigger signal outputted by the detecting device. By the automatic synchronous-exposure control, it can acquire a clear X-ray image by only one proper X-ray exposure operation, thus prevent the human body from the needless X-ray radiation caused by the multiple X-ray exposures, and also improve the service efficiency of the equipment.

The present invention further provides an X-ray imaging method, including: through selecting one of a distance between a filament and an anode target surface of an X-ray tube and a distance between a filament cage and the anode target surface of the X-ray tube, enabling the X-ray tube to produce X-ray at a tube voltage between 25-50 kV so as to be used in X-ray imaging for child at age of 0-3.

In the X-ray device or the X-ray imaging method, a range of the distance between the filament and the anode target surface is 13~15 mm, and a range of the distance between the filament cage and the anode target surface is 8~10 mm.

In the X-ray device or the X-ray imaging method, includes: an X-ray filter comprising of a metal with 0.5 to 2.5 mm aluminum-equivalent, to filter the X-ray whose energy is low and which is not able to provide clear image so as to output soft X-ray of 25 kV to 50 kV; wherein the X-ray tube uses a molybdenum target or a rhodium target; and wherein the X-ray device produces X-ray at the tube voltage of: 25 kV -50 kV suitable for child at age of 0-1; 30 kV-40 kV suitable for child at age of 1-2; 35 kV-50 kV suitable for child at age of 2-3.

BRIEF DESCRIPTION OF THE DRAWINGS

The above and the other objects and features will become more apparent from the following description, taken in conjunction with the accompanying drawings.

DETAILED DESCRIPTION OF THE PREFERRED EMBODIMENTS

Figure 1:
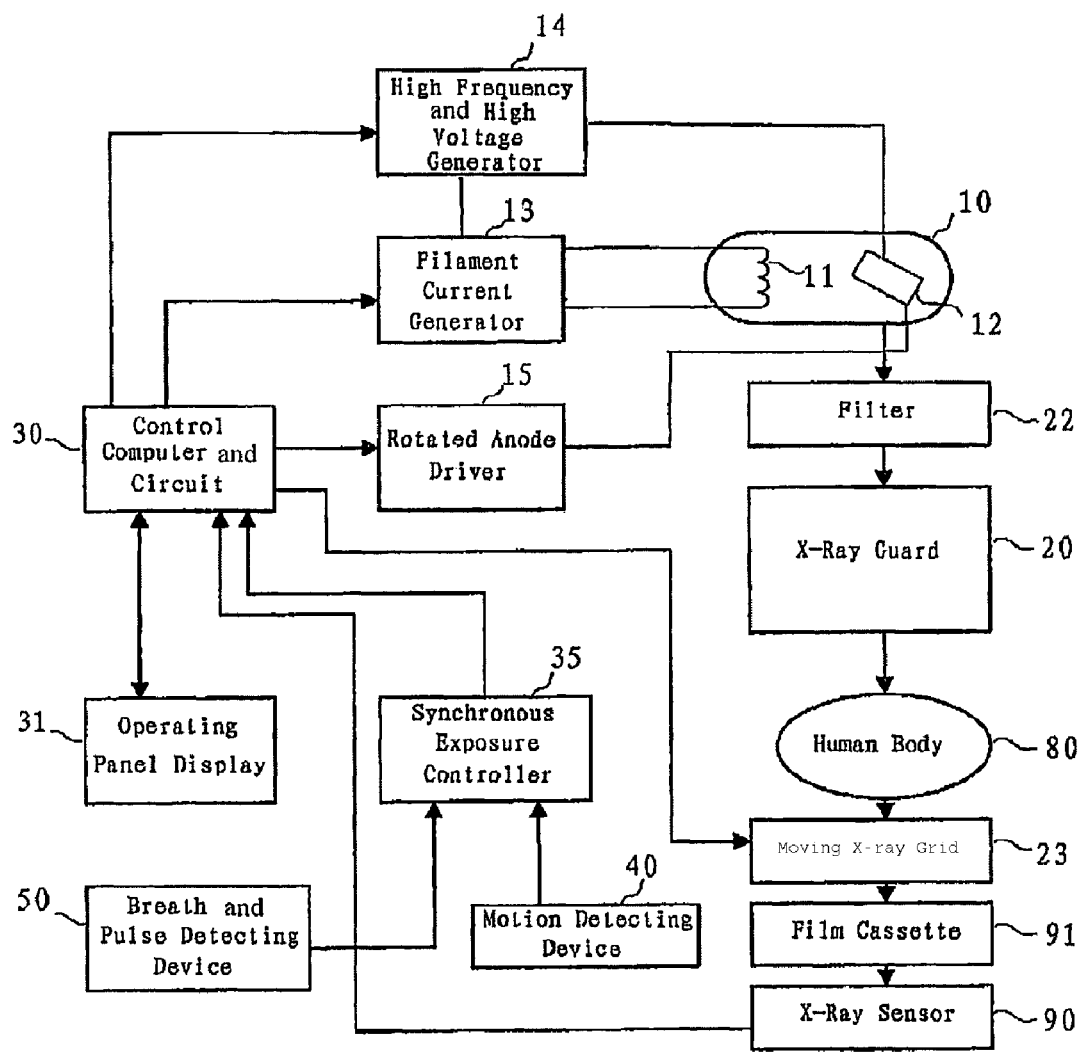
FIG. 1 is a schematic diagram showing an X-ray device according to the present invention.

Hereinafter, description will be made in detail to embodiments of the present invention with reference to the accompanying drawings. Throughout the accompanying drawings, like reference numerals refer to same or similar elements.

FIG. 1 is a schematic diagram showing an X-ray device according to the present invention. Referring to FIG. 1, the X-ray device according to the present invention includes an X-ray tube 10 comprising molybdenum target or rhodium target 12. The filament 11 in the X-ray tube 10 is heated by current generated by a current generator 13, thereby produces active electrons which bombard the target 12 to produce X-ray under acceleration by a voltage applied by a high voltage generator 14 to the filament 11 and the target 12. The X-ray irradiate on a part of tissues of a subject 80 (e.g., human body) after energy thereof is filtered through an X-ray filter 22. The X-ray attenuated by the human body 80 passes a moving X-ray grid 23 to filter scattered radiation which blurs an image, and then irradiates on a film cassette 91 having an X-ray intensifying screen and holding X-ray sensitive film and on the X-ray sensor 90, so that the X-ray film is imaged by exposure and the dose signal of the imaging X-ray can be obtained.

Figure 9:
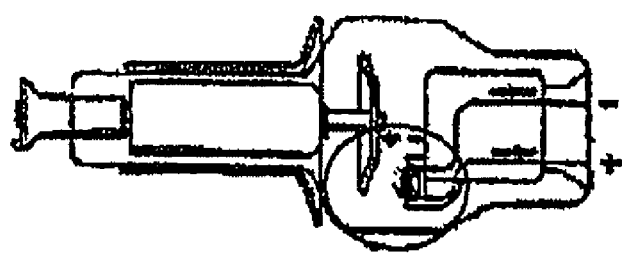
FIG. 9 shows a schematic diagram of construction of the rotated anode X-ray device according to one embodiment of the present invention.
Figure 10:
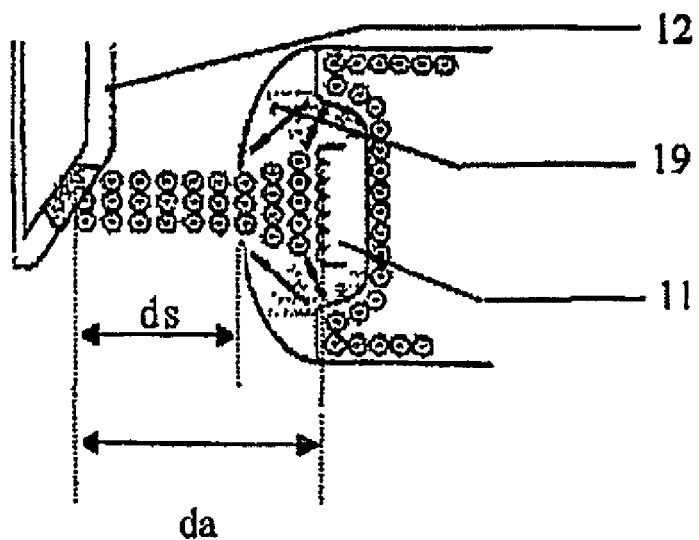
FIG. 10 is a diagram for enlarging a part of FIG. 9 for illustrating distances from a filament and a filament cage to the anode target surface.

FIG. 9 shows a schematic diagram of construction of the rotated anode X-ray device according to one embodiment of the present invention, and FIG. 10 is a diagram for enlarging a part indicated by a circle in FIG. 9 for illustrating distances from a filament and a filament cage to the anode target surface. Referring to FIG. 9 and FIG. 10, the distance from the filament 11 to the anode target surface 12 in the X-ray tube 10 is effected by the factors such as used tube voltage, size and shape of the filament cage 19, vacuum degree in the tube etc. However, there is little difference among the manufacturing processes of all tube factories in the world, and the size and the shape of the filament cage 19 and the vacuum degree in the tube are substantially the same, so the distance between the filament of the X-ray tube and the anode target surface is dependent on magnitude of the used tube voltage. If the distance is too large, in the case of exposure at a low voltage, the X-ray can not be output or the dose of the X-ray is smaller; if the distance is too small, in the case of exposure at a high voltage, the flashover occurs.

As shown in FIG. 10, ds is the distance between the filament cage and the anode target surface, and da is the distance between the filament and the anode target surface. In general, da−ds=5 mm, the distance ds between the filament cage and the anode target surface is often used in engineering generally.

In a mammary X-ray tube, the distance da between the filament and the anode target surface is 11~12 mm, the distance ds between the filament cage and the anode target surface is 6~7 mm, and corresponds to a tube voltage 20~35 kV; in a general X-ray tube, the distance da between the filament and the anode target surface is 17~25 mm, the ds is 12~20 mm, and corresponds to a tube voltage 50~150 kV. In the tube of the present invention, the distance da between the filament of and the anode target surface is 13~15 mm (the optimum value is 14 mm), the ds is 8~10 mm (the optimum value is 9 mm), and corresponds to a tube voltage 25~50 kV.

As an example in the practice, the da taking 13, 14 or 15 mm, the ds taking 8, 9 or 10 mm and the tube voltage taking 25, 30, 35, 40 or 50 kV can acquire clear images for the pediatric X-ray imaging.

The present invention uses a 0.5-2.5 mm aluminum-equivalent metal plate X-ray filter 22, and can filter the X-ray under 25 kV, which is useless for imaging to increase ratio of soft X-ray of 25-50 kV to total X-ray. The X-ray in such a range is especially applicable to the X-ray imaging for the child at the age of 0-3, wherein using the tube voltage 25 kV-50 kV is suitable for a child at age of 0-1, 30 kV-40 kV is suitable for a child at age of 1-2, and 35 kV-50 kV is suitable for a child at age of 2-3. As an example in the practice, the X-ray filter 22 can use 0.5, 1.0, 1.5 or 2.5 mm aluminum-equivalent metal plate.

The X-ray device according to the present invention further includes: a control computer and circuit 30 which may control a high voltage generator 14 and a current generator 13 to generate a stable X-ray within a certain energy range and may start the moving X-ray grid 23 synchronously with the exposure to filter the scattered radiation which blurs the images so as to make the images clear; an operating panel display 31 to input an operation command to the control computer and circuit 30 and display the exposure parameters; and a synchronous exposure controller 35 which, according to a motion status obtained from a motion detecting device 40 and a breath/pulse status obtained from a breath/pulse detecting device 50, outputs exposure trigger signals to the control computer and circuit 30 which controls the high voltage generator 14 to operate to trigger an exposure operation. The X-ray device of the present invention further includes an automatic exposure controller (included in the control computer and circuit 30), which controls an exposure stop time based on a stop condition preset by the control computer and circuit 30 and according to an X-ray dose signal received from an X-ray sensor 90, thereby determines exposure duration together with the synchronous exposure controller 35 under the control of the control computer and circuit 30. The X-ray sensor 90 can employ an ionization chamber or a photoelectric multiplier tube (PMT) to supply an electrical signal of the X-ray intensity subject to amplification processing to the automatic exposure controller.

Further, the target 12 may be a fixed anode or rotated anode. The rotated anode is driven to rotate by a rotated anode driver 15, started by the control computer and circuit 30 before an exposure, so as to increase the thermal capacity of the target surface, increase the exposure allowance current and reduce the exposure time, thereby improve an imaging clearness.

Details of a motion synchronous exposure control are illustrated below taken in conjunction with FIG. 2-5. It is a fully automatic synchronous exposure controller which is designed according to a characteristic that the child is often in motion, and which automatically identifies a motion status of the child's body and outputs an exposure trigger signal upon determining the child is in a preset still status according to the identified motion status. It can use only one proper operation to complete the X-ray exposure to form image clearly.

Figure 2:
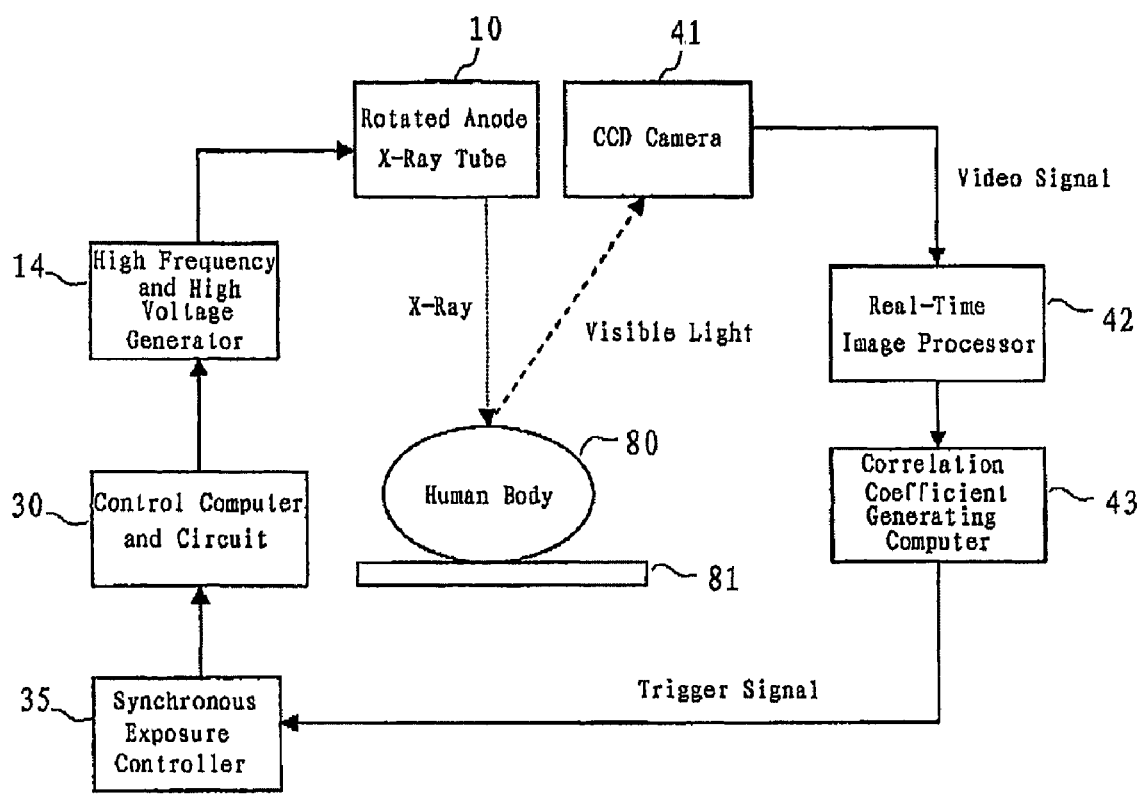
FIG. 2 illustrates realizing synchronous-exposure control with an image determining method.

FIG. 2 illustrates realizing the synchronous-exposure control with an image determining method, wherein functions of the motion detecting device 40 in FIG. 1 are implemented by a CCD camera 41, a real-time image processor 42 and a correlation coefficient generating computer 43. Through a natural visible light, the CCD camera captures the status images of a subject of a human body 80 on the table 81, and then the status images of the human body captured by the CCD camera are input as video signals to the real-time image processor 42, in which a continuous image processing operation in real-time is made. The real-time image processor 42 inputs the continuously processed image data into the correlation coefficient generating computer 43, and obtains the correlation coefficients of the continuous images. The correlation coefficient generating computer 43 is generally composed of high-speed processor (DSP) to meet the requirement of calculating the correlation coefficients of the continuous images. When the correlation coefficient is higher than a preset value (for example, 90%), which indicates that the motion status of the human body is in a preset still status, and generates a trigger signal and supplies the trigger signal to the synchronous exposure controller 35. Then, the exposure trigger signal is output to the control computer and circuit 30 which controls the high frequency and high voltage generator 14 to operate to start to irradiate the X-ray, thereby starts to perform the X-ray exposure.

Figure 3:
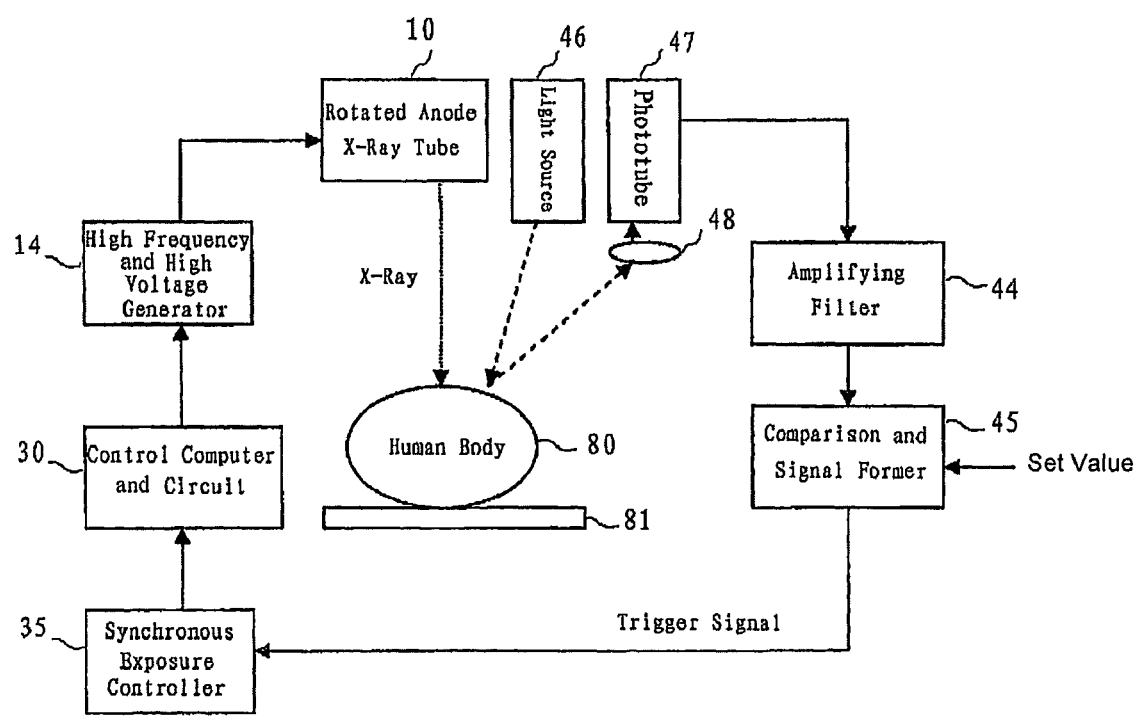
FIG. 3 illustrates realizing synchronous-exposure control with a photoelectric determining method.

FIG. 3 illustrates realizing the synchronous-exposure control with a photoelectric determining method, wherein functions of the motion detecting device 40 in FIG. 1 are implemented by a light source 46, a phototube 47, an imaging lens 48, an amplifying filter 44 and a comparison and signal former 45. The light source 46 is used to irradiate the subject of the human body 80 on the table 81, the lights reflected by the human body 80 form an image by the imaging lens 48, and then the image of the human body 80 is projected onto the photoelectric element (phototube) 47. The phototube 47 converts the projected image light signals to electrical signals which are processed by an amplifying/filtering circuit (the amplifying filter) 44 for filtering a direct current component representing a contribution of a environment status, and a variation signal of the irradiated image of the human body are obtained. When this signal is smaller than a preset value, which indicates that the motion status of the human body is in a preset still status, the comparison and signal former 45 compares this signal the preset value, and produces a trigger signal subject to a signal forming. Similar to the consequent processes as described in FIG. 2, the produced trigger signal is supplied to the synchronous exposure controller 35, which produces the exposure trigger signal to trigger the control computer and circuit 30 to perform the X-ray exposure. The light generated from the light source 46 may be a visible light or infrared light (including laser light). To improve an antidisturbance ability against the light from the circumstance around, the light is usually modulated and demodulated, i.e., frequency or phase of the light from the light source is modulated and is demodulated at a light detecting end.

Figure 4:
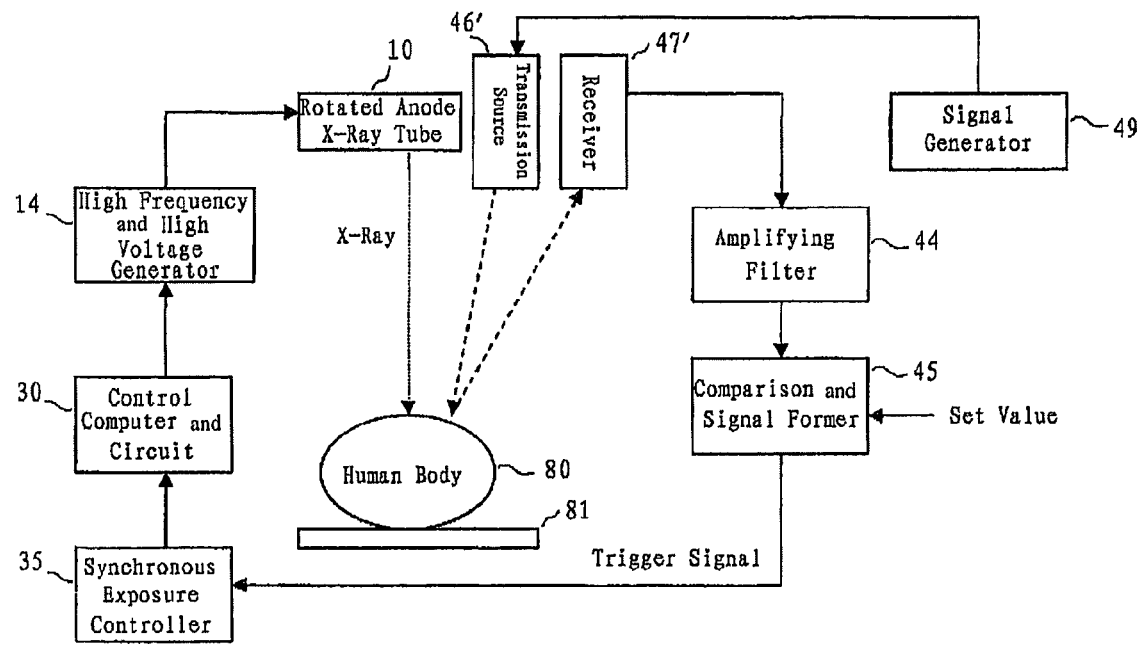
FIG. 4 illustrates realizing synchronous-exposure control with a radar method.

FIG. 4 illustrates realizing the synchronous-exposure control with a radar method, wherein functions of the motion detecting device 40 in FIG. 1 are implemented by a transmission source 46', a signal generator 49, a receiver 47', an amplifying filter 44 and a comparison and signal former 45. Wherein microwave signals are generated by the signal generator 49 and irradiate on the human body 80 on the table 81 through the transmission source 46'. The microwave signals reflected by the human body 80 are received by the receiver 47', in which the reflected microwave signals are converted to electrical signals which are processed by an amplifying/filtering circuit (the amplifying filter) 44 for filtering a direct current component representing a contribution of an environment status, and variation signals of the motion status of the human body are obtained. When this signal is smaller than a preset value, which indicates that the motion status of the human body is in a preset still status, the comparison and signal former 45 compares this signal with the preset value, and produces a trigger signal subject to a signal forming. Similar to the consequent processes as described in FIG. 2, the produced trigger signal is supplied to the synchronous exposure controller 35, which produces the exposure trigger signal to trigger the control computer and circuit 30 to perform the X-ray exposure. The signals generated from the signal generator 49 may be microwaves or ultrasound waves or other electromagnetic wave signals applicable for being implemented by the circuit shown in FIG. 4.

In addition to the above-mentioned image determining method, photoelectric determining method, microwave radar method and ultrasound wave radar method, the specific implementing methods of the synchronous-exposure control (also referred to as "motion synchronous-exposure control") related to avoid the effect of human body motion status, may involve a mechanical shake method (not shown). Its principle is as follows: a high sensitivity shake sensor is disposed on the table 81; when the human body moves, the sensor outputs a shake signal, the amplitude of which reflects the shake degree of the human body motion. When this signal is smaller than a preset value, which indicates that the motion status of the human body is in a preset still status, the trigger signal is produced. It can be seen that the specific implementing methods of the synchronous-exposure control as described are not limited to those as listed above, those skilled in the art can implement them with other proper variation such as a capacitance induction method etc.

Figure 6A:
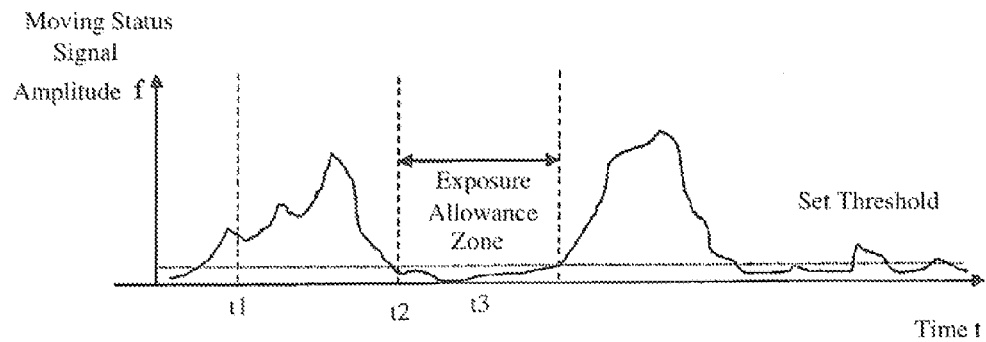
FIG. 6A illustrates a graph of a relative amplitude f of a body moving status signal over time t when the synchronous-exposure control is performed according to the present invention; and FIG. 6B

FIG. 6A illustrates a graph of a relative amplitude f of a body moving status signal over time t when the synchronous-exposure control is performed according to the present invention. After an instruction is input through the control computer and circuit 30 to start the exposure procedure, under the control of the control computer and circuit 30, the high frequency and high voltage generator 14 does not operate immediately but the above-mentioned motion detecting device 40 is used to detect the motion status of the child's body 80, as at time t1 in FIG. 6A. When the child's body 80 stops moving temporarily, as at time t2 in FIG. 6A, an output of the motion detecting device 40 (i.e., a motion status signal) reaches an allowable range of the preset value, for example, less than a set threshold (except the image determining method), the motion detecting device 40 outputs an exposure trigger signal (more detailed control refers to the illustration of FIG. 2-4) to the control computer and circuit 30, which controls the high frequency and high voltage generator 14 to operate to perform the exposure operation. At a certain time in an exposure allowance zone in FIG. 6A, for example, time t3, the automatic exposure controller of the X-ray device controls the stop of the exposure.

With the motion synchronous-exposure control, a moving artificial images on the film caused by the frequent moving of the human body especially a infant or child's body can be removed, so that it can acquire a clear X-ray image through only one X-ray exposure, thus prevent the human body from the needless X-ray radiation caused by the multiple X-ray exposures, and also improve the service efficiency of the equipment.

Figure 5:
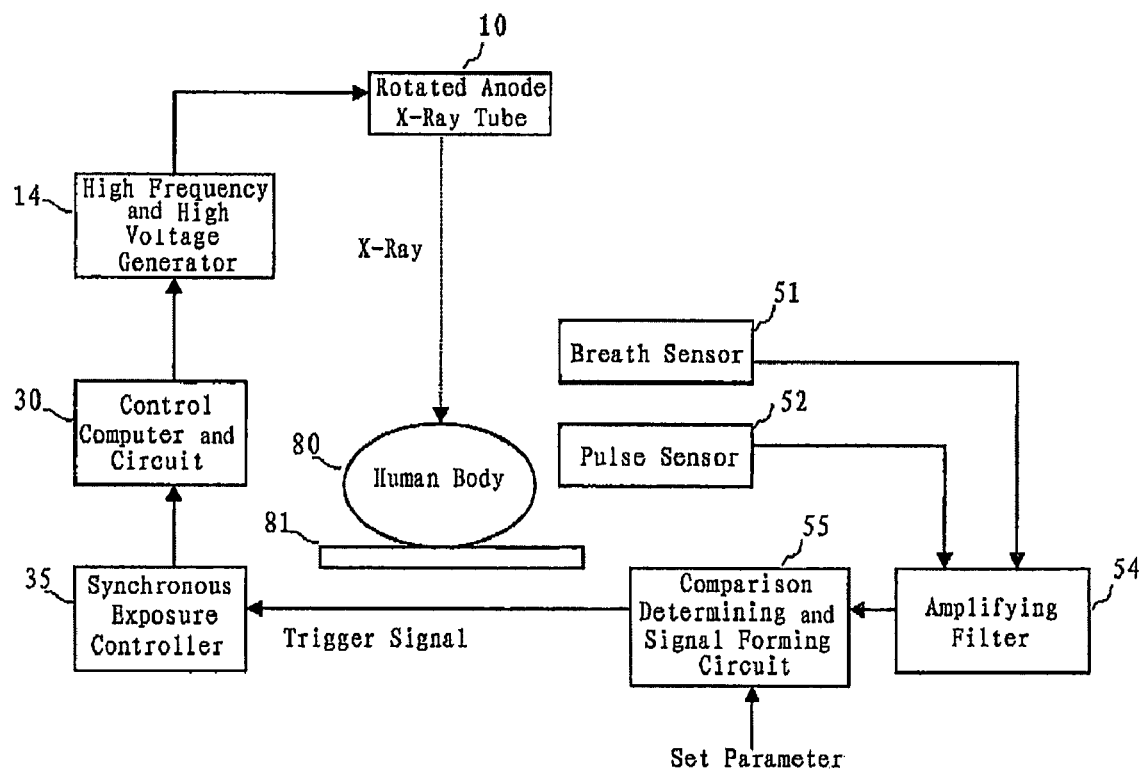
FIG. 5 illustrates realizing breath/pulse synchronous-exposure control according to the present invention.

FIG. 5 illustrates realizing breath/pulse synchronous-exposure control according to the present invention, wherein functions of the breath/pulse detecting device 50 in FIG. 1 are implemented by a breath sensor 51, a pulse sensor 52, an amplifying filter 54 and a comparison determining and signal forming circuit 55.

Referring to FIG. 5, a breath status of a subject of a human body 80 on the table 81 is sensed by the breath sensor 51. An electrical signal sensed by the breath sensor 51, which indicates the breath status of the subject of the human body 80, is processed by the amplifying/filtering circuit (the amplifying filter) 54 for filtering a direct current component representing interference, and then a variation signal of the breath status of the human body is obtained. When a stable status of the breath transition is reached, the trigger signal is generated, as described below in conjunction with FIG. 6B. Then, still similar to the consequent processes as described in FIG. 2, the generated trigger signal is supplied to the synchronous exposure controller 35, which produces the exposure trigger signal to trigger the control computer and circuit 30 to perform the X-ray exposure. The breath sensor may be a breath pressure sensor or a breath sound sensor.

Similarly, the pulse sensor 52 senses a cardiac activity status of the human body, i.e., a cardiac activity graph status. An electrical signal sensed by the pulse sensor 52, which indicates the cardiac activity graph status of the subject of the human body 80 on the table 81, is processed by the amplifying/filtering circuit (the amplifying filter) 54 for filtering a direct current component representing interference, and then a variation signal of the pulse of the human body is obtained. When a stable status of the heartbeat is reached, the trigger signal is generated, as described below in conjunction with FIG. 6C. Then, still similar to the consequent processes as described in FIG. 2, the generated trigger signal is supplied to the synchronous exposure controller 35, which produces the exposure trigger signal to trigger the control computer and circuit 30 to perform the X-ray exposure. The pulse sensor may be an infrared photoelectric pulse sensor, an electrocardiogram pulse sensor or a cardiac sound pulse sensor.

Figure 6B:
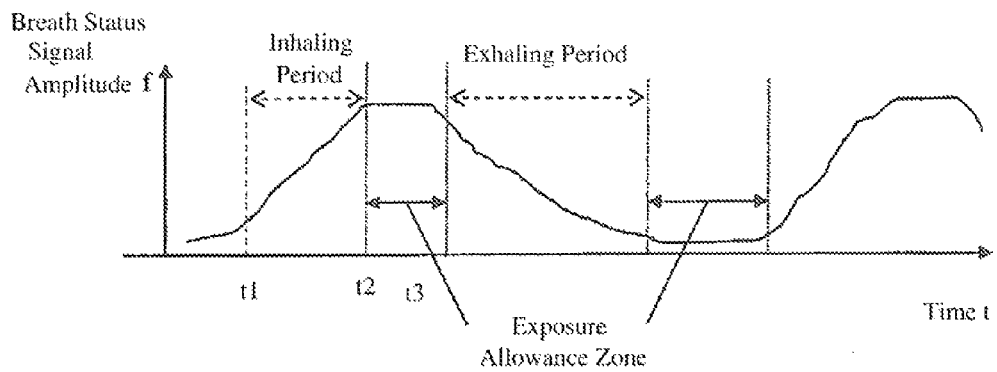
FIG. 6C shows graphs of a relative amplitude f of a breath status signal and a relative amplitude b of a pulse signal over time t when the breath synchronous-exposure control and the pulse synchronous-exposure control are performed according to the present invention, respectively.
Figure 6C:
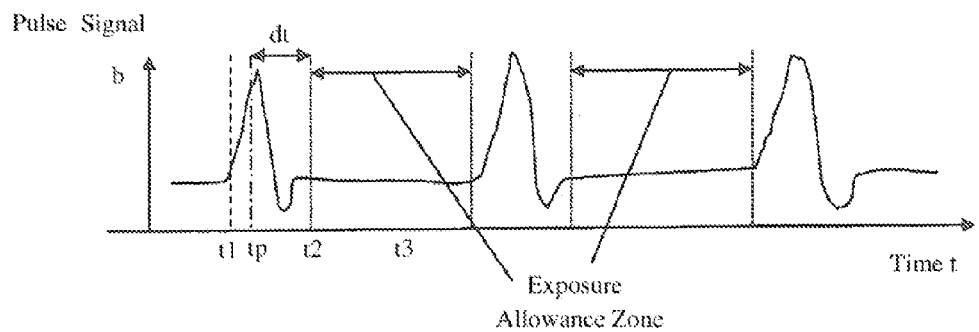

Referring to FIG. 6B and FIG. 6C, the breath synchronous exposure control and the pulse synchronous exposure control according to the present invention are further illustrated in the following. FIG. 6B and FIG. 6C shows graphs of a relative amplitude f of a breath status signal and a relative amplitude b of a pulse signal over time t when the breath synchronous-exposure control and the pulse synchronous-exposure control are performed according to the present invention, respectively. A man is not always exhaling or inhaling, and there are relative halt periods at the transition of the two motions. As shown in FIG. 6B, in a human breath status signal sensed by the breath sensor 51, there are relative stable period at the transition of breath between a inhaling period in which the relative amplitude f increases with time t and a exhaling period in which the relative amplitude f increases with time t, as well as between the inhaling period and the exhaling period, such as an exposure allowance zone shown in FIG. 6B. Also as shown in FIG. 6C, in a human pulse signal obtained by being sensed via the pulse sensor 52 and being processed, a clearance between two heart beat pulses is also the relative stable status of the human body. For example, at time t1 in FIGS. 6B and 6C, after the exposure procedure is started by inputting instructions through the control computer and circuit 30, under the control of the control computer and circuit 30, the high frequency and high voltage generator 14 does not operate immediately but the breath and pulse status of the human body 80 is detected using the breath sensor 51 and the pulse sensor 52. In FIG. 6B, a comparison determination are made by the comparison determining and signal forming circuit 55 so as to generate the trigger signal subject to signal formation based on a set parameter, for example, reaching a peak or valley for a certain time as a determination of being in the above-mentioned relative stable periods at the transition of the breath. Also in FIG. 6C, the comparison determination are made by the comparison determining and signal forming circuit 55 so as to generate the trigger signal subject to signal formation based on a set parameter, for example, a time tp reaching a peak value plus a delay time dt, as a trigger time t2=tp+dt, i.e., a start time of the relative stable status of the pulse. The delay time dt is used to avoid the unstable period within a certain time following the peak value of the pulse signal, and the proper value thereof can be determined according to the statistic of the heart beat measurement. The above-mentioned generated trigger signal is passed to the synchronous exposure controller 35, and then the control computer and circuit 30 controls the high frequency and high voltage generator 14 to operate to perform the X-ray exposure. Then, at a certain time in the exposure allowance zone in FIGS. 6B and 6C, for example time t3, the automatic exposure controller of the X-ray device controls the stop of the exposure.

With the breath synchronous exposure control and the pulse synchronous exposure control, the moving artificial images caused by the breath and the heart beat pulse can be removed, so that a clearer X-ray image can be acquired.

According to the practical requirements of the X-ray imaging, the above-mentioned moving synchronous exposure control, breath synchronous exposure control and pulse synchronous exposure control can be used separately or in combination. For example, the three exposure trigger signals are determined with time overlap so that the three exposure trigger conditions are all satisfied and a clearest image can be acquired. Since the exposure time is short up to 0.01~0.5 sec, it is relatively easy to satisfy two of the three conditions in practice.

Figure 7:
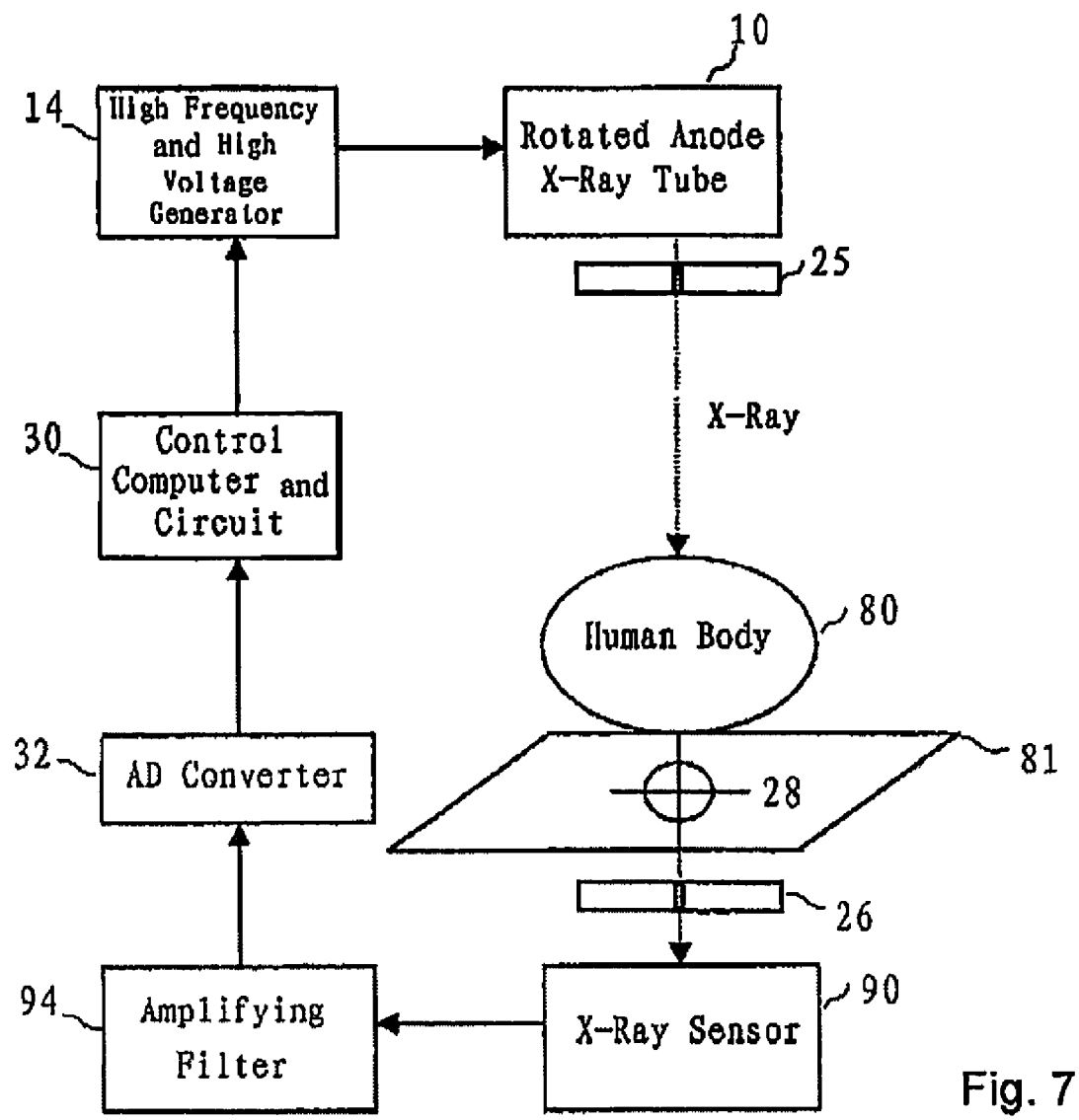
FIG. 7 is a schematic diagram of configuration of an X-ray device realizing a method of measuring bone density using X-ray dual energy method according to the present invention.

Referring to FIG. 7, illustrated below is the method measuring bone density using X-ray dual energy method with the X-ray device according to the present invention. FIG. 7 is a schematic diagram of configuration of an X-ray device realizing the method measuring the bone density using the X-ray dual energy method, wherein only the main parts are shown and detailed descriptions of the functions of the parts with the same reference numerals as those in FIG. 1 are omitted for simplification. Referring to FIG. 7, a small-bore collimator 25 is disposed on the outlet of the X-ray tub 10, through which the X-ray irradiates on bone tissue parts of the human body 80 on the table 81, which can be realized by aiming at a collimation label 28 on the table 81. The X-ray passing through the bone of the human body reaches the X-ray sensor 90 (such as PMT) through the collimation label 28 and a second small-bore collimator 26 under the table 81. The first small-bore collimator 25 and the second small-bore collimator 26 are used to collimate the X-ray. The control computer and circuit 30 control the high frequency and high voltage generator 14 such that the X-ray tube 10 outputs respectively X-ray of 28 kV and 48 kV in time division, and the filament current of the X-ray tube is fixed (for example, 5 mA). The X-ray sensor 90 transmits two measured signals through an amplifying filter 94 to an AD converter 32 (which can be integrated into the control computer and circuit 30), and then to the control computer and circuit 30 to be processed for displaying a density value of the bone.

A calculating method of the density value of the bone is: measuring the two absorptivities of the X-ray with different energies passing through the bone and the soft-tissue, and then solving the following equation:

$$I_1 = I_{01}\exp(-u_{1B}M_B - u_{1S}M_S)$$

$$I_2 = I_{02}\exp(-u_{2B}M_B - u_{2S}M_S)$$

where $I_{01}$, $I_{02}$ are incident intensities of the two types of the X-ray respectively, $I_1$, $I_2$ are measured intensities after transmission respectively, $M_B$, $M_S$ are surface densities of the bone (B) and the soft-tissue (S) respectively, $u_B$, $u_S$ are absorbance attenuated coefficients of the bone (B) and the soft-tissue (S) respectively;

to get the bone density $M_B$ (unit: g/cm$^2$) as:

$$M_B = (u_{1S}J_2 - u_{2S}J_1)/(u_{1S}u_{2B} - u_{2S}u_{1B})$$

where $J_1 = \ln(I_{01}/I_1)$, $J_2 = \ln(I_{02}/I_2)$.

The function of measuring the bone density can be used to diagnose the calcific status of the child, for example, diagnosing child acalcerosis and child rachitis etc. Under the control of the control computer and circuit 30, a X-ray film exposure status and a bone density measuring status of the device can be switched via a selection switch. In the bone density measuring status, the control computer and circuit 30 displays the bone density data obtained by measuring and calculating.

Figure 8:
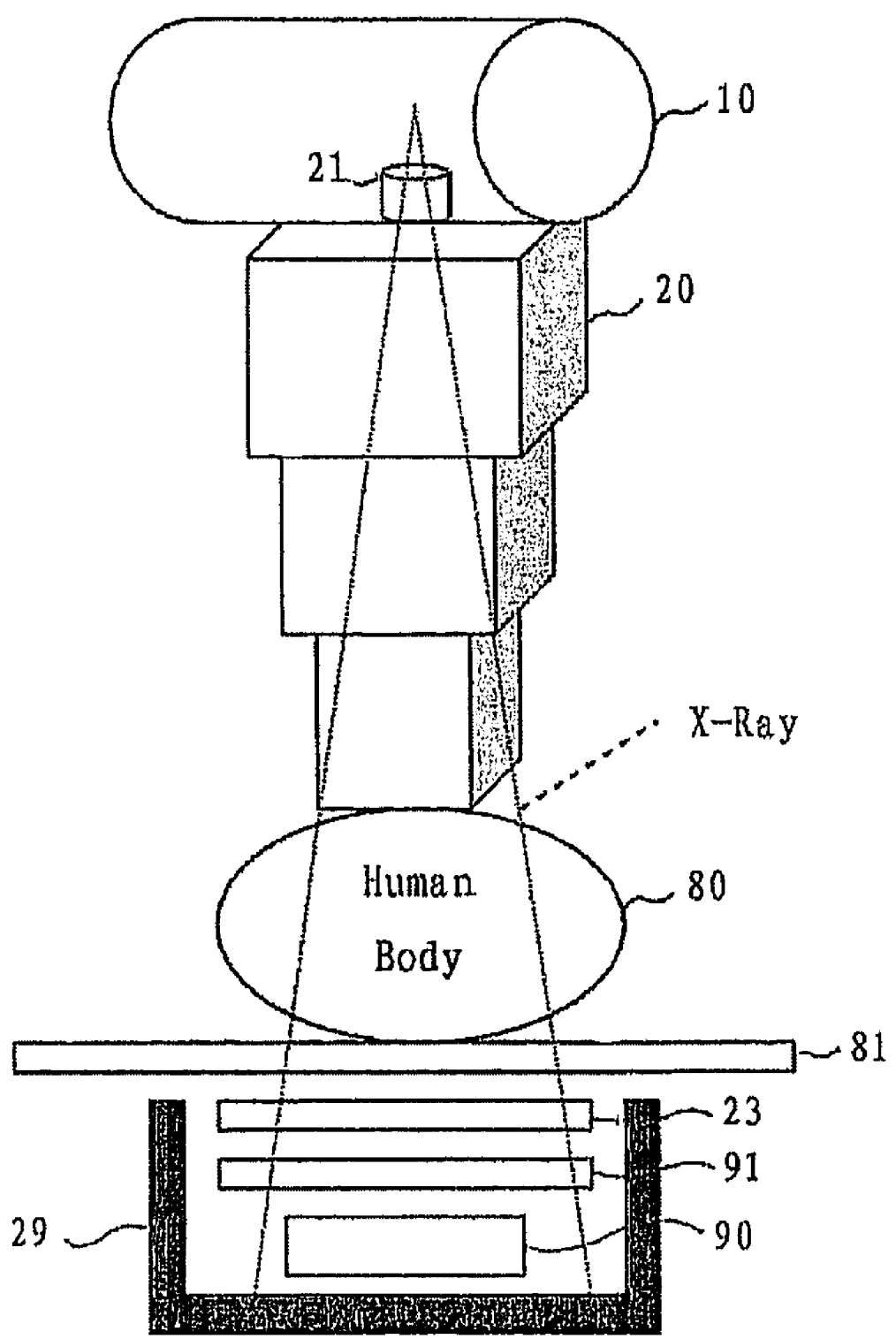
FIG. 8 is a schematic diagram of configuration of an X-ray device including an X-ray guard according to the present invention.

Referring to FIG. 8, illustrated is an X-ray guard device further employed by the X-ray device according to the present invention. FIG. 8 is a schematic diagram of configuration of an X-ray device including the X-ray guard according to the present invention, wherein only the main parts are shown and detailed descriptions of the functions of the parts with the same reference numerals as those in FIG. 1 are omitted for simplification. Referring to FIG. 8, an irradiation-scope controller 21, such as a diaphragm made by lead, is disposed on the outlet of the X-ray tube 10 to control the irradiation range (irradiation-scope) of the X-ray. An extendable lead protection cavity 20 is disposed below the irradiation-scope controller 21 and between the irradiation-scope controller 21 and the human body 80 on the table 81, and can extend to touch the part being irradiated of the human body 80 such that the X-ray only irradiates within the irradiation-scope of the part to be imaged on a patent's body, and the other parts are protected from the X-ray by the guard device, so that the other parts of the patent's body and the circumstance around are not irradiated by the X-ray at all. After passing through the human body 80, the X-ray passes the motive filtering-ray grid 23 to filter the scattered radiation which is bad to imaging, and then irradiates on the film cassette 91 and the X-ray sensor 90 to complete the X-ray exposure for imaging. A lead shield mask 29 with one panel removed is disposed on the bottom of the table 81 such that the irradiation-scope controlled by the irradiation-scope controller 21 is completely contained within the lead shield mask 29. The lead shield mask 29 could be any proper shape such as cuboid or cylinder, which prevents the residual X-ray passing through the table 81 from leakage.

The X-ray guard device according to the present invention makes the leakage radiation and the scattered radiation lower and has more perfect radial protection than the normal X-ray device, such that operators and parents accompanying children can get better X-ray guard.

It is noted that the X-ray guard device according to the present invention can be applied to the normal X-ray device to improve the ability of the X-ray guard. The present invention is not limit to the above-mentioned embodiments, and various variations and modifications can be made without apart from the scope of the invention.

INDUSTRIAL APPLICABILITY

The above-mentioned design principle of the present invention can be applied to a pediatric X-ray device as well as a pediatric C-arm and a pediatric bed-side X-ray device etc.

The invention claimed is:

1. An X-ray device, comprising:
an X-ray tube;
a filament;
an anode target surface; and
a filament cage;
wherein a distance between the filament and the anode target surface of the X-ray tube has a range of 13~15 mm or a distance between the filament cage and the anode target surface of the X-ray tube has a range of 8~10 mm, which produces X-ray at a tube voltage between 25-50 kV so as to be used in X-ray imaging for child at age of 0-3.

2. The X-ray device of claim 1, further comprising:
an X-ray filter comprising a metal with 0.5 to 2.5 mm aluminum-equivalent, to filter the X-ray whose energy is low and which is not able to provide clear image so as to output soft X-ray of 25 kV to 50 kV;
wherein the X-ray tube uses a molybdenum target or a rhodium target; and
wherein the X-ray device produces X-ray at the tube voltage of: 25 kV-35 kV suitable for child at age of 0-1; 30 kV-40 kV suitable for child at age of 1-2; 35 kV- 50 kV suitable for child at age of 2-3.

3. The X-ray device of claim 1, further comprising:
a detecting device to automatically identify status of a subject of a human body and output an exposure start trigger signal when determining that the status of the human body is in a preset still status or a relative stable status according to the identified status of the human body;
a synchronous-exposure controller to perform automatic synchronous-exposure according the trigger signal outputted by the detecting device.

4. The X-ray device of claim 3, wherein the detecting device includes:
a CCD camera to capture images of the status of the human body;
a real-time image processor to perform a continuous image processing to the images of the status captured by the CCD camera;
a correlation coefficient generating computer to calculate correlation coefficient of the continuous images, and generate a trigger signal when the correlation coefficient of the continuous images is higher than a preset value.

5. The X-ray device of claim 3, wherein the detecting device includes:
a light source to generate visible light or infrared light to irradiate the human body;
an imaging lens to receive light reflected from the human body and form an image of the human body;
a phototube to convert a light signal of the image projected by the imaging lens into an electrical signal;
an amplifying filtering circuit to amplify and filter the electrical signal converted by the phototube for filtering a direct current component to obtain a variation signal of the irradiated image of the human body; and a comparison and signal forming circuit to compare the obtained variation signal of the irradiated image of the human body with a preset value, and generate a trigger signal subject to signal formation when the variation signal is lower than the preset value.

6. The X-ray device of claim 3, wherein the detecting device includes:

a transmission source to transmit electromagnetic waves or ultrasonic waves to the human body;

a receiver to receive the waves reflected from the human body and convert the reflected waves into electrical signals;

an amplifying filtering circuit to amplify and filter the electrical signals converted by the receiver for filtering direct current components to obtain variation signals of position status of the human body; and a comparison determination and signal forming circuit to compare the obtained variation signal of the position status of the human body with a preset value, and generate a trigger signal subject to signal formation when the variation signal is lower than the preset value.

7. The X-ray device of claim 3, wherein the detecting device includes:

a breath sensor to sense breath status of the human body and form it into electrical signal;

an amplifying filtering circuit to amplify and filter the electrical signal from the breath sensor for filtering a direct current component to obtain a variation signal of the breath status of the human body; and a comparison determination and signal forming circuit to make a comparison determination to the obtained variation signal of the breath status of the human body, and generate a trigger signal subject to signal formation when determining the variation signal is in a stable breath period according to a set parameter.

8. The X-ray device of claim 3, wherein the detecting device includes:

a pulse sensor to sense pulse status of the human body and form it into an electrical signal;

an amplifying filtering circuit to amplify and filter the electrical signal from the pulse sensor for filtering a direct current component to obtain a variation signal of the pulse of the human body; and a comparison determination and signal forming circuit to make a comparison determination to the obtained variation signal of the pulse of the human body, and generate a trigger signal subject to signal formation when determining the variation signal is in a stable pulse period according to a set parameter.

9. The X-ray device of claim 1, wherein:

two small-bore collimators are disposed respectively on an X-ray outlet along the direction of X-ray radiation and under a table on which a subject of a human body is placed, and a collimation label is disposed on the table so that the X-ray is collimated by the two small-bore collimators and the collimation label.

10. The X-ray device of claim 9, wherein:

by measuring absorptivities of the X-ray with two different energy $I_{01}$, $I_{02}$ passing through bones and soft-tissues and the absorbance attenuated energy $I_1$, $I_2$, a bone density MB (with unit of $g/cm^2$) is calculated as follows:

$$M_B = (u_{1S}J_2 - u_{2S}J_1)/(u_{1S}u_{2B} - u_{2S}u_{1B})$$

$$J_1 = \ln(I_{01}/I_1), J_2 = \ln(I_{02}/I_2)$$

where the subscript 1 and 2 represent related values corresponding to the two different incident energy respectively, $u_B$, $u_S$ are absorbance attenuated coefficients of the bone B and the soft-tissue S respectively.

11. The X-ray device of claim 1, further comprising:

an X-ray guard, wherein disposed between an outlet of the X-ray tube and a subject of a human body is an extendable lead protection cavity, which extends to touch the part of the human body being irradiated such that the X-ray only radiates within a range of the part being irradiated, and the other parts are protected from the X-ray by the lead protection cavity.

12. The X-ray device of claim 11, the X-ray guard further includes:

a cuboid lead shield mask with a top panel removed, which is disposed on the bottom of a table on which the human body is placed, such that the residual X-ray passing through the table are prevented from emitting.

13. A method of X-ray imaging, comprising:

providing an X-ray device, the X-ray device comprising an X-ray tube, a filament, an anode target surface, and a filament cage;

selecting one of a distance between the filament and the anode target surface of the X-ray tube and a distance between the filament cage and the anode target surface of the X-ray tube; and enabling the X-ray tube to produce X-ray at an X-ray tube voltage between 25-50 kV so as to be used in X-ray imaging for child at age of 0-3;

wherein a range of the distance between the filament and the anode target surface is 13~15 mm, and a range of the distance between the filament cage and the anode target surface is 8~10 mm.

14. The method of X-ray imaging of claim 13, wherein:

an X-ray filter comprising a metal with 0.5 to 2.5 mm aluminum-equivalent is used to filter the X-ray whose energy is low and which is not able to provide clear image so as to output soft X-ray of 25 kV to 50 kV;

wherein the X-ray tube uses a molybdenum target or a rhodium target; and wherein the X-ray device produces X-ray at the tube voltage of: 25 kV-35 kV suitable for child at age of 0-1; 30 kV-40 kV suitable for child at age of 1-2; 35 kV-50 kV suitable for child at age of 2-3.

* * * * *